(12) United States Patent
Pierce et al.

(10) Patent No.: US 8,444,512 B2
(45) Date of Patent: May 21, 2013

(54) SCENT DISPERSING APPARATUS

(75) Inventors: William Fred Pierce, DeQuincy, LA (US); Tony James Latiolais, St. Martinville, LA (US)

(73) Assignee: Rac Em Bac, L.L.C., DeQuincy, LA (US)

( * ) Notice: Subject to any disclaimer, the term of this patent is extended or adjusted under 35 U.S.C. 154(b) by 0 days.

(21) Appl. No.: 13/199,901

(22) Filed: Sep. 13, 2011

(65) Prior Publication Data
US 2012/0153037 A1  Jun. 21, 2012

Related U.S. Application Data

(63) Continuation-in-part of application No. 12/928,772, filed on Dec. 16, 2010.

(51) Int. Cl.
*F42B 6/04* (2006.01)
(52) U.S. Cl.
USPC .......................................... 473/578; 473/581

(58) Field of Classification Search .................. 473/578, 473/581, 582
See application file for complete search history.

(56) References Cited

U.S. PATENT DOCUMENTS

| | | | |
|---|---|---|---|
| 4,726,584 A | 2/1988 | Bishop |
| 5,123,567 A | 6/1992 | Anderson |
| 5,836,842 A | 11/1998 | McLearan |
| 6,174,251 B1 | 1/2001 | Lemote |
| 6,450,905 B1 | 9/2002 | Edlund |
| 7,601,084 B2 | 10/2009 | Martin |
| 2008/0051231 A1 | 2/2008 | Everett |
| 2010/0031945 A1 | 2/2010 | Shaffer et al. |

*Primary Examiner* — John Ricci
(74) *Attorney, Agent, or Firm* — Schultz & Associates, P.C.

(57) ABSTRACT

An animal attractant, such as a liquid scent can be dispersed from a frangible housing by attaching the housing to an arrow and firing an arrow in a designated area frequented by animals. The housing has large fins secured about outer periphery of the housing, enlarging the impact surface of the housing and preventing the housing from being embedded in the soil. As a result, the animal attractant is dispersed above the ground and is not lost in the soil.

40 Claims, 5 Drawing Sheets

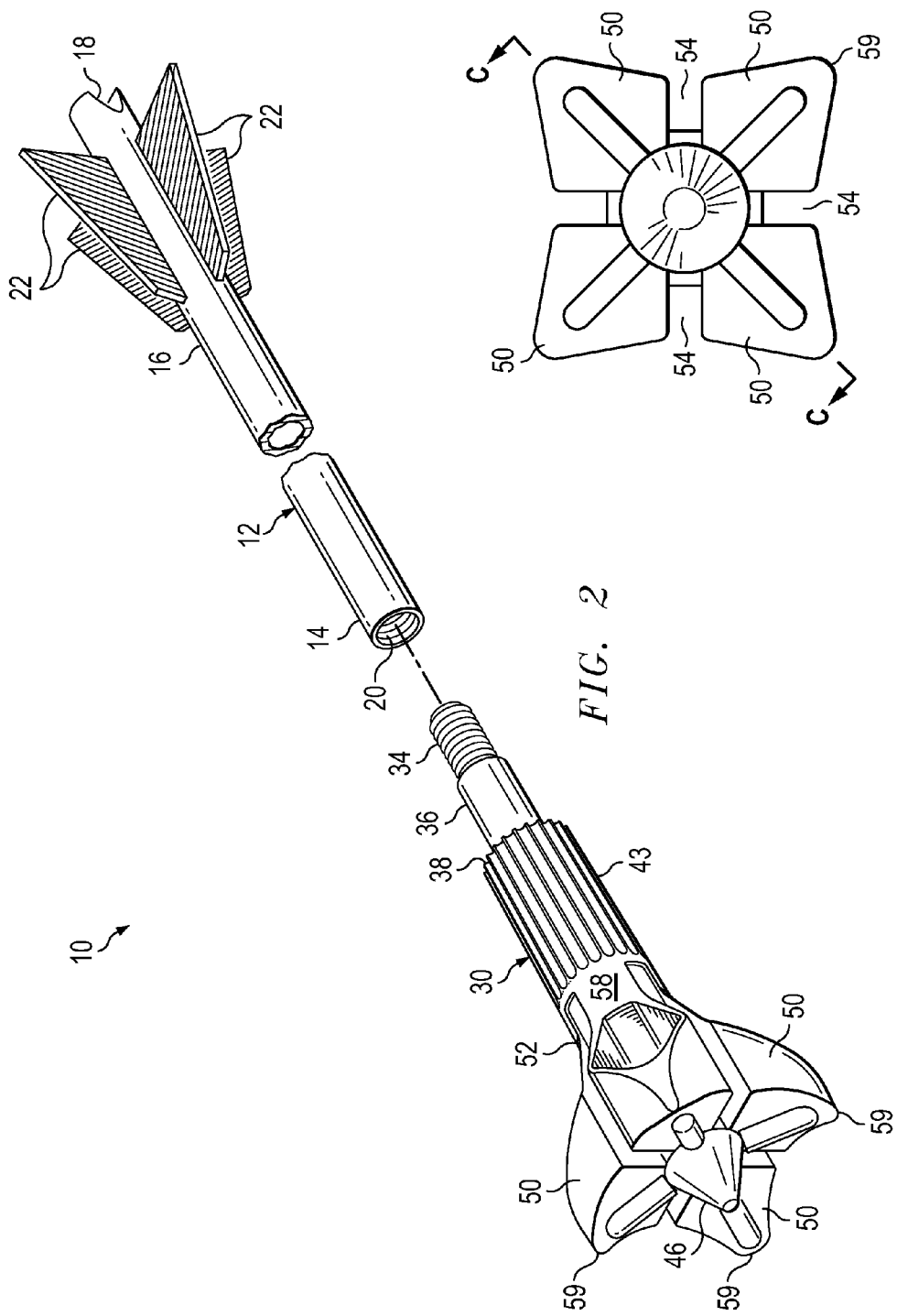

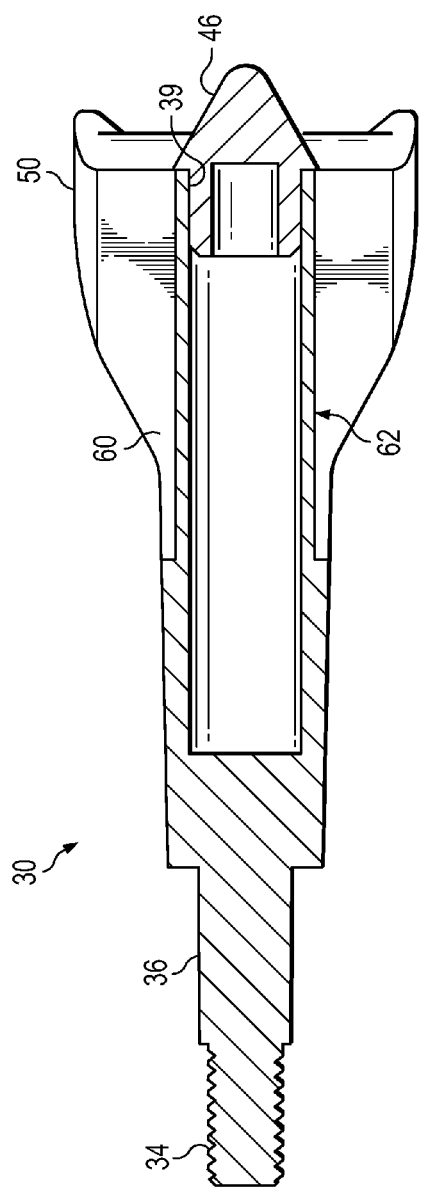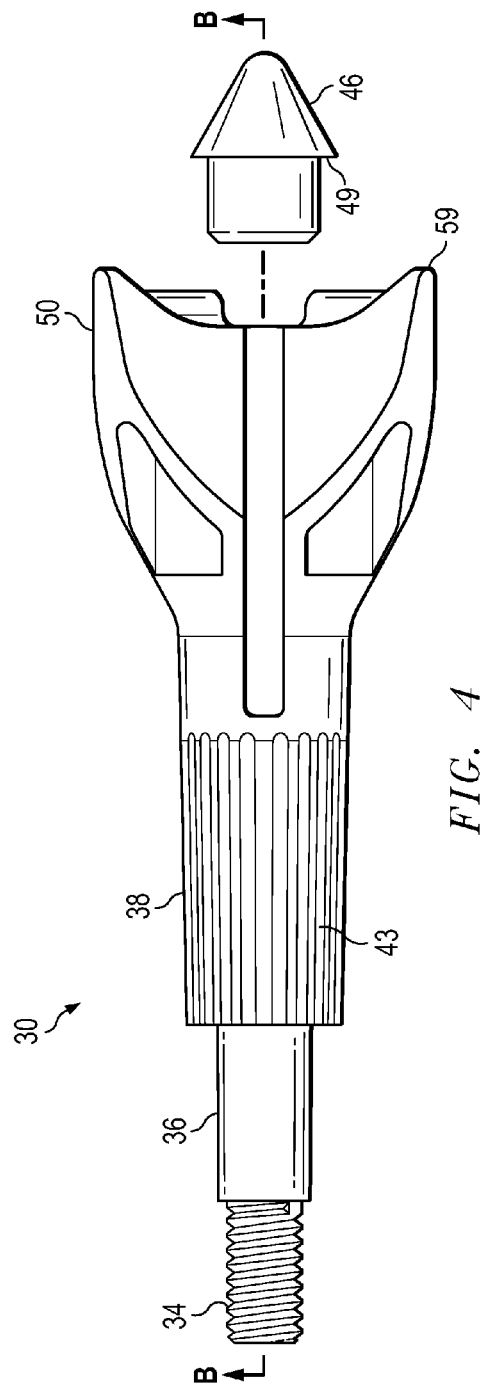

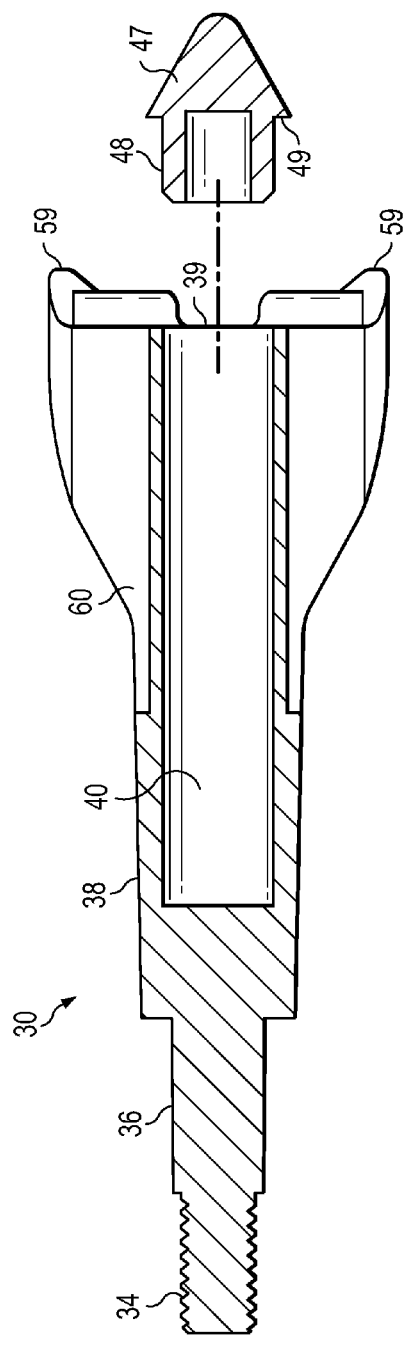
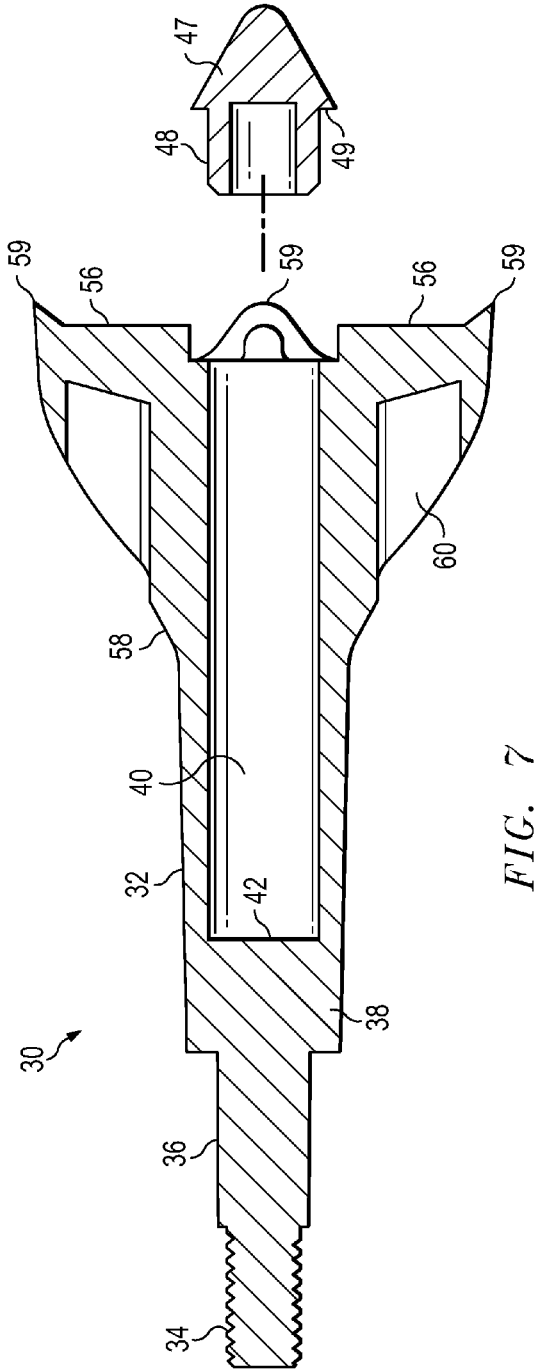

SCENT DISPERSING APPARATUS

CROSS-REFERENCE TO RELATED APPLICATIONS

This application is a continuation-in-part of my co-pending application Ser. No. 12/928,772 filed on Dec. 16, 2010 entitled "Scent Dispersing Apparatus," the full disclosure of which is incorporated by reference herein and priority of which is hereby claimed.

BACKGROUND OF THE INVENTION

This invention relates to hunting equipment, and more particularly to an apparatus for dispersing liquid scent substance, such as a deer attractant.

In the sport of game hunting it is conventional for a hunter to select a spot believed to be in a path or other area where the game is likely to be and wait for the animal in a tree or other hiding place. Typically, a hunting stand is erected on a tree above the expected travel path of the animals where a hunter can stay without scaring the animal and without leaving a human scent. To improve the hunter's odds, an attractant such as the scent of such animal may be left in the area so that other animals of the species would investigate it and while doing so, offer more target opportunities for the hunter.

Furthermore, the hunter hiding in a tree has to descend to the ground and spread the scent manually in the target area. A conventional alternative was to wet a rag or other absorbent material, tie the rag to an arrow and then fire the arrow from the tree stand. However, such approach suffers from major disadvantages—the liquid can be spilled on the hunter or his clothes. Moreover, some of the scent is dispersed during the arrow flight and very little of the liquid reaches the ground.

To solve this problem, the sporting industry developed several solutions, some of which is to use an arrow with pre-loaded scent containers. The containers are designed to open or break upon impact with the ground and dispense the liquid scent onto an absorbent medium positioned on the hollow cavity of an arrow. However, the use of absorbent medium necessarily diminishes the amount of scent dispersed in the desired area, thus requiring more than one arrow to be fired in order to establish an attractive site for the animal.

My co-pending application discloses an improved scent dispersing arrowhead where a hollow body has a pair of opposing cutouts through which an animal attractant, such as liquid scent can exit the hollow body. The hollow body is configured to retain a frangible liquid-scent containing capsule. A plunger is configured to slide into the scent capsule enclosure and cause rapture the scent-containing capsule upon impact of the plunger with a solid surface, such as ground, rock or tree limb. While this arrowhead has distinct advantages over conventional scent dispersing arrows, it was discovered that a narrow forward tip of the arrowhead tends to at least slightly penetrate the soil and thus disperse a portion of the scent liquid into the soil.

The present invention contemplates elimination of drawbacks associated with conventional scent dispersing arrows and provision of an arrowhead that has greater contact surface and causes the body of the arrowhead to fracture upon impact with the ground.

SUMMARY OF THE INVENTION

It is, therefore, an object of the present invention to provide a scent dispersing arrow for use in game hunting.

It is another object of the invention to provide a scent dispersing arrow that causes a scent container to be fractured upon contact with the ground, thus dispersing the liquid scent in the desired hunting area.

It is a further object of the invention to provide a scent dispersing arrow that is configured to carry an enlarged heavy forward portion for better control of the arrow flight.

These and other objects of the invention are achieved through a provision of a scent dispersing apparatus comprising a scent dispersing assembly configured for attachment to an arrow that can be fired from a tree stand or other concealed area in a hunting position. The scent dispersing assembly comprises a frangible hollow housing defining a liquid-scent enclosure. The housing has a generally cylindrical hollow body and a plurality of fins secured about an outer periphery of the hollow body and extending outwardly therefrom. The fins resemble buttresses secured to a forward end of the housing. The fins are adapted to substantially increase outer dimensions of a forward end of the housing and prevent the housing from being embedded into the soil upon impact. The hollow body is configured to fracture upon impact with a solid surface releasing the liquid animal attractant.

BRIEF DESCRIPTION OF THE DRAWINGS

Reference will now be made to the drawings, wherein like parts are designated by like numerals, and wherein

FIG. 2 is a perspective view of the scent dispersing arrow of this invention.

FIG. 3 is a sectional view of the scent dispersing arrow of the present invention.

FIG. 4 is a cutaway view of the apparatus of the present invention, with the cap detached.

FIG. 5 is a sectional view taken along lines B-B of FIG. 3.

FIG. 6 is an end view of the apparatus of the present invention.

FIG. 7 is a sectional view taken along lines C-C of FIG. 5.

DETAIL DESCRIPTION OF THE INVENTION

Figure 1:
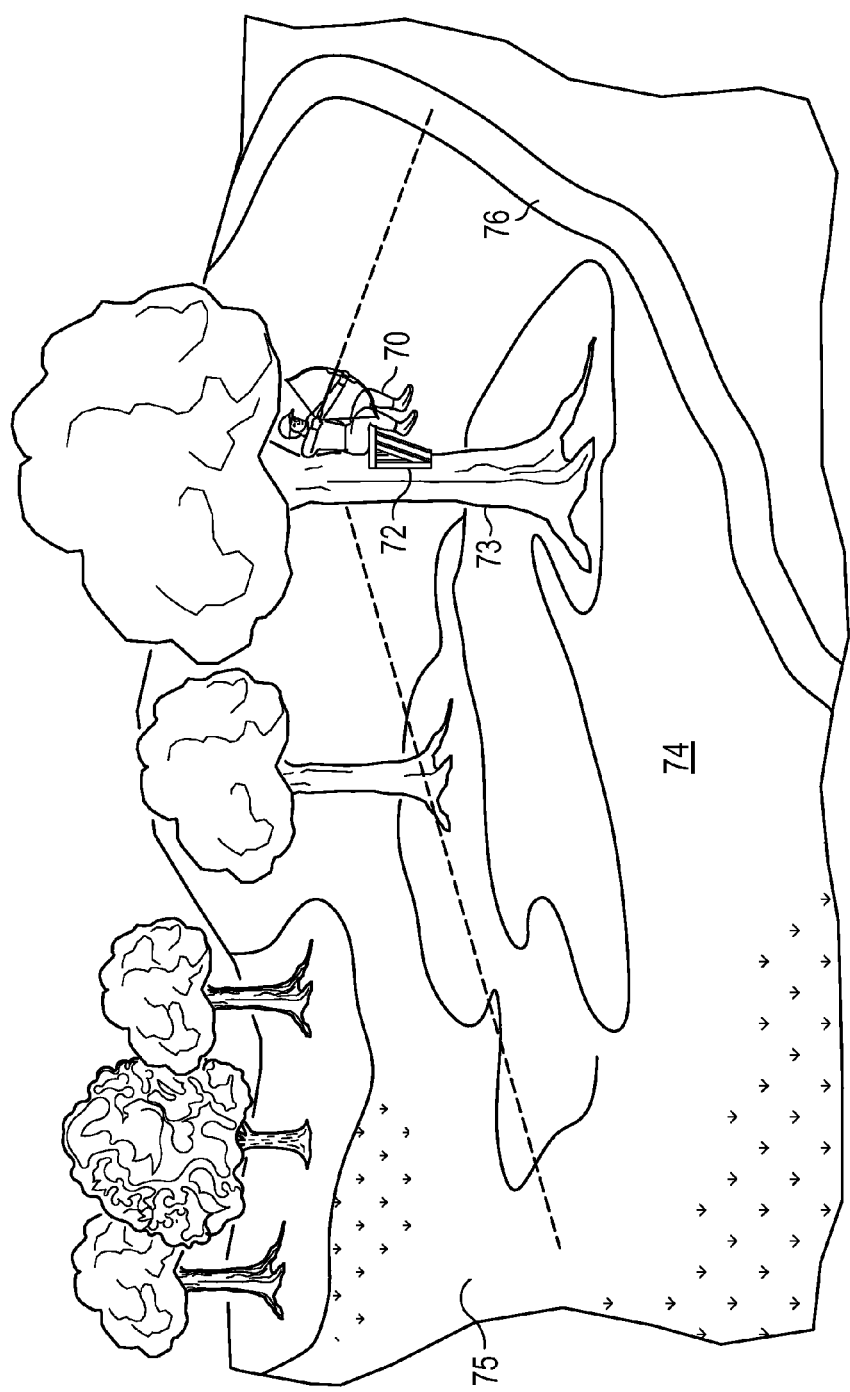
FIG. 1 is a schematic view of the hunting location where the scent dispersing arrow of this invention is used.

Turning now to the drawings in more detail, numeral 10 designates the scent dispersing arrow in accordance with the present invention. The arrow 10 comprises an elongate cylindrical shaft 12. The arrow shaft 12 has an open forward end 14 and a closed distant end 16. A nock 18 is formed in the distant end 16 to accommodate a bow string. The forward end 14 of the shaft 12 is open and a threaded insert 20 is positioned therein. Conventional vanes 22 (FIG. 2) may be attached to the arrow shaft 12 adjacent the distant end 16. The arrow 10 may have two or three vanes 22 equidistantly spaced about the circumference of the arrow shaft 12.

A scent dispersing assembly 30 is detachably secured on the arrow shaft 12. The scent dispersing assembly comprises a housing 32 having a proximate threaded portion 34. The threads of the proximate portion are configured to matingly detachably engage with the threads of the insert 20. The housing 32 also comprises an intermediate portion 36, which can be formed as a cylindrical member, as a transitional member between the proximate threaded portion 34 and a distant portion 38.

The distant portion capsule enclosure 38 is formed as a generally cylindrical hollow member having a diameter greater than the threaded portion 34 and the intermediate portion 36. Of course, the housing 32 can be formed as a cylindrical body having the same diameter from one end to the other, with one end having external threads similar to the threads on the threaded portion 34. If desired, the exterior surface of the distant portion 38 can be provided with a plurality of ridges 43, which increase friction of the exterior surface and facilitate a better grip of the scent dispersing assembly by a user. This feature is particularly beneficial when the user threadably engages the scent dispersing assembly 30 with the arrow shaft 12.

In one aspect of the invention, the distant portion 38 defines an internal chamber 40, which extends through a major part of the distant portion 38. The distant portion 38 has an open end 39 opposite the threaded portion 34. The opposite end 41 of the chamber 40 is closed by a transverse inner wall 42. It is envisioned that the chamber 40 is sized to retain about 1000 mg of synthetic or natural scent that is designed to attract animals being hunted during a particular hunting season.

A detachable cap 46 is configured to close the open end 39 after a scented liquid is loaded into the chamber 40. The cap 46 has a generally conical first part 47 and a generally cylindrical second part 48. The second part 48 of the cap 46 can be made hollow, as shown in FIGS. 5 and 7. The exterior dimensions of the second part 48 are such that the second part 48 frictionally engages interior sidewall of the chamber 40, fitting into the open end 39 when the cap 46 is engaged with the open end 39 of the distant portion 38. A shoulder 49 formed between the first part 47 and the second part 48 of the cap 46. As can be seen in FIG. 3, the shoulder 49 engages the outer end 39 of the distant portion 38 when the cap is fitted into the opening of the end 39.

A plurality of fins 50 is equidistantly secured about a forward part 52 of the distant portion 38. The fins 50 resemble buttresses surrounding the cylindrical distant portion 38. The fins 50 are separated by channels 54 which are designed to improve aerodynamics of the arrow 10. As can be seen in the drawings, the fins 50 substantially increase the outer dimensions of the distant end 38. In one aspect of the invention, each fin 50 has an outwardly flaring end plate 56 unitary formed with an attachment member 58, which secures the fin 50 to the exterior of the distant portion 38. The end plate 56 is provided with a narrow point 59 that extends as the most forward point of the housing 32.

The fin 50 may be formed hollow as a shell or with an open proximate end 60. As can be seen in the drawings, the proximate end 60 is formed opposite the end plate 56 of the fin 50. In one aspect of the invention, combined surface area of the end plates 56 is almost twice as large as the diameter of the cylindrical distant portion 38 without the fins 50. The fins 50 can be triangular in cross-section or resemble a rhombus. Although four such fins are shown in the drawings, it will be realized that other number of fins can be used as well.

The distant portion 38 is formed as a thin-walled enclosure for the scent dispersing liquid that is loaded into the chamber 40. In one of the preferred embodiments the cylindrical wall 62 is about 0.03" (0.76 mm) thick to encourage the distant portion 38 to fracture upon impact with a solid surface, which can be ground or a tree trunk. The diameter of the chamber 40 can be about 0.25" (6.35 mm). The distance between a pair of opposing points 59 of the fins 50 can be about 1" (25.4 mm); the length of the scent dispersing assembly can be about 2.38" (60.45 mm); and the length of the distant portion 38 can be about 1.7" (43.18 mm). Of course, these dimensions are exemplary and other dimensions can be selected by the manufacturer if desired.

The scent dispersing assembly 30 can be made from a variety of frangible materials, such as for instance thin plastic. The arrow shaft can be made of rigid plastic or other conventional material. It is envisioned that the scent dispersing assembly 30 can be manufactured and sold separately from the arrow 12, and can be adapted for use with any type of arrow. A kit containing a plurality of the scent dispersing assemblies 30 can be sold as a separate item. In operation, a hunter 70 is positioned in a tree stand 72, which is elevated above ground 74. Usually, the tree stand 72 is erected in a location adjacent a food plot 75 or trail 76 frequented by the animals, such as deer. Preferably, the area around the tree 73 where the tree stand is positioned contains minimal human scent that can be discerned by the hunted animal.

The hunter 70 selects one scent dispersing assembly 30, which has been pre-loaded with the desired scent in the chamber 40. The chamber 40 is closed with the cap 46. The hunter then threadably engages the scent dispersing assembly 30 with the arrow shaft 12 using the matching threads 20 in the shaft 12 and the external threads on the threaded portion 34. Once the scent dispersing assembly 30 is securely engaged with the arrow shaft 12, the hunter fires the arrow aiming either toward the food plot 75 or to a trail 76. The trajectory of the arrow flight is shown in phantom lines in FIG. 1.

As the arrow hits the ground 74 the wide end plates 56 of the fins 50 do not allow the scent dispersing assembly 30 from embedding in the soil. As a result, the liquid scent is not lost in the soil but rather dispersed on the surface. The pointed ends 59 of the fins 50 can be partially embedded in the soil. The impact force, made stronger by the weight of the liquid in the chamber 40 and the fins 50 is transmitted to the body of the distant portion 38.

Figure 8:
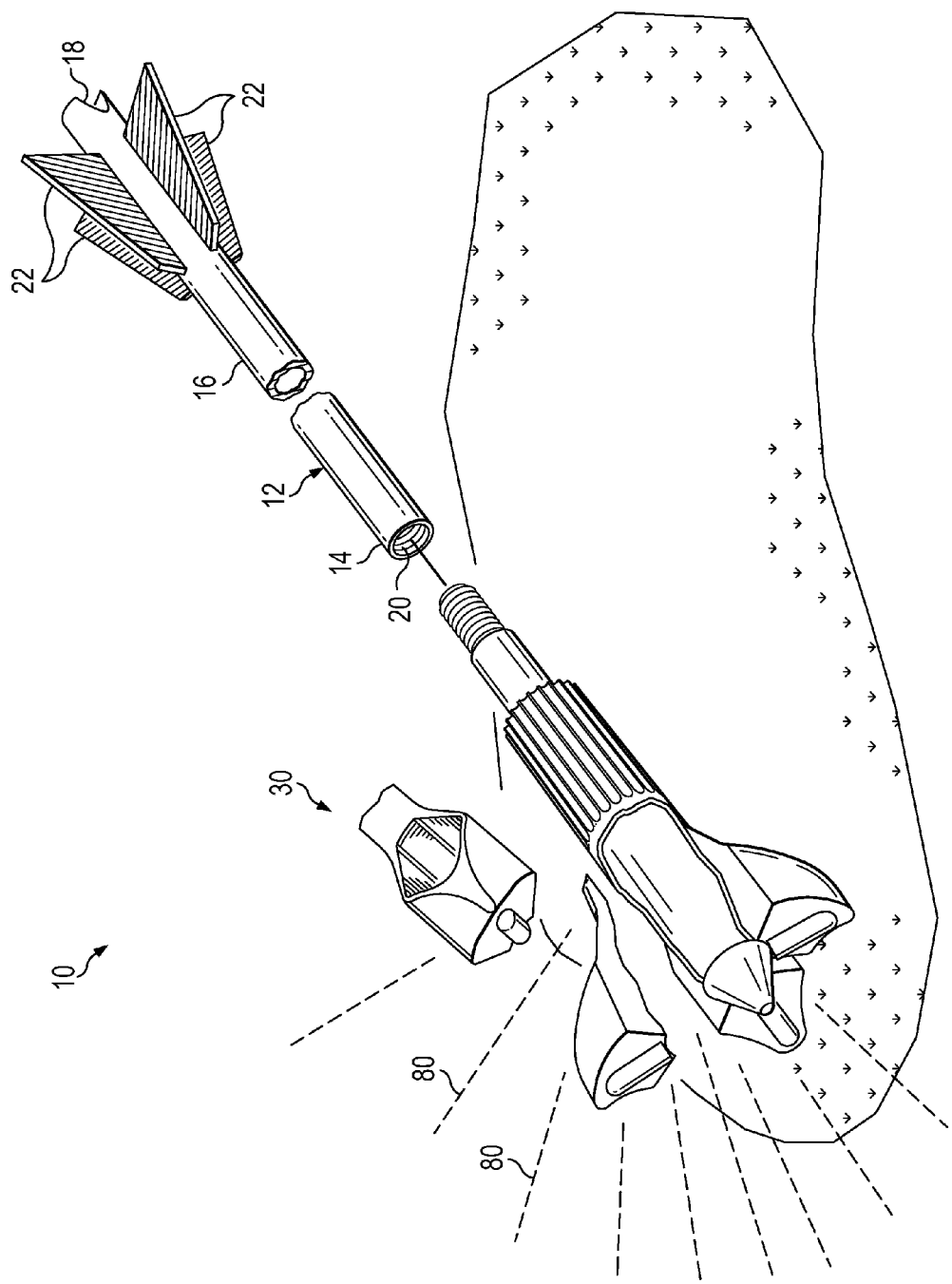
FIG. 8 illustrates the scent dispensing arrow broken upon impact with the ground.

The forceful impact of the fins with a solid surface transmits the impact force to the housing 32 causing the thin walls to fracture and disperse the liquid in the area of the impact. As a consequence the liquid scent exits the housing 32 in a fan-like fashion, as illustrated in phantom lines 80 in FIG. 8. Following the hunt, the hunter 70 can retrieve the arrow, disengage the broken housing 32 from the arrow shaft 12 and engage another assembly 30 with liquid scent with the shaft 12. The arrow shaft 12 can thus be used numerous times.

The scent dispersing arrow and the scent dispersing assembly of the present invention prevent spills of the liquid scent on the hunter or hunter's closing by using an encapsulated item. The hunter can select the most advantageous point for scent dispersal from an elevated position, without leaving undesirable human scent on the deer trail. The targeted delivery of the liquid scent to the most desired area ensures maximum exposure thereof to the game.

Many changes and modifications can be made in the design of the present invention without departing from the spirit thereof. I, therefore, pray that my rights to the present invention be limited only by the scope of the appended claims.

We claim:

1. A scent dispersing apparatus, comprising:
a scent dispersing assembly configured for attachment to an arrow, said scent dispersing assembly comprising a frangible housing defining a liquid-scent enclosure, said housing having a generally cylindrical hollow body and a plurality of fins secured about an outer periphery of the hollow body and extending outwardly therefrom, said plurality of fins increasing the outer dimensions of a forward end of the housing, wherein each of said plurality of fins comprises an outwardly flaring front plate and an attachment member, where the attachment member is integrally formed with the front plate and the housing, said hollow body being configured to fracture upon impact with a solid surface releasing liquid scent.

2. The apparatus of claim 1, wherein the hollow body defines a chamber adapted to retain an animal attractant.

3. The apparatus of claim 1, wherein the housing comprises a proximate portion configured for detachable engagement with the arrow, a distant portion carrying the plurality of fins and an intermediate portion formed between the proximate portion and the distant portion.

4. The apparatus of claim 3, wherein said proximate portion is provided with threads configured for matching engagement with threads formed in the arrow.

5. The apparatus of claim 3, wherein said distant portion is formed as a thin-walled enclosure defining a chamber configured to retain a liquid animal attractant.

6. The apparatus of claim 5, wherein the chamber is defined by a sidewall having about 0.76 mm in thickness.

7. The apparatus of claim 3, wherein said distant portion has an open forward end, and wherein a cap is detachably engaged with the open end.

8. The apparatus of claim 3, wherein the distant portion has an exterior surface, and wherein a plurality of friction-enhancing ridges is formed on the exterior surface.

9. The apparatus of claim 3, wherein the distant portion has a pre-determined outer diameter, and wherein a combined surface area of the outwardly flaring front plates of the plurality of fins is greater than the outer diameter of the distant portion.

10. The apparatus of claim 3, wherein each said outwardly flaring front plate is provided with a narrow point extending forwardly of the distant portion.

11. The apparatus of claim 1, wherein the housing is formed from a fracturable material.

12. The apparatus of claim 1, wherein said plurality of fins is equidistantly secured to the exterior surface of the housing, and wherein channels are formed between adjacent fins.

13. A scent dispersing apparatus, comprising:
an elongated arrow shaft having a first end provided with threads;
a scent dispersing assembly having a threaded end configured for detachable engagement with the first end of the arrow shaft, said scent dispersing assembly comprising a frangible housing formed with an inner chamber configured for retaining a pre-determined quantity of a liquid animal attractant and a plurality of fins secured on a forward end of the housing and extending outwardly therefrom, wherein each of said plurality of fins comprises an outwardly flaring front plate and an attachment member, where the attachment member is integrally formed with the front plate and the housing, said housing being configured to be fractured upon forceful impact of at least one of the plurality of fins with a solid surface thereby releasing the animal attractant.

14. The apparatus of claim 13, wherein the housing comprises a proximate portion configured for detachable engagement with the arrow, a distant portion carrying the plurality of fins and an intermediate portion formed between the proximate portion and the distant portion.

15. The apparatus of claim 14, wherein said distant portion is formed as a thin-walled enclosure defining a chamber configured to retain a liquid animal attractant.

16. The apparatus of claim 15, wherein the chamber is defined by a sidewall having about 0.76 mm in thickness.

17. The apparatus of claim 14, wherein said distant portion has an open forward end, and wherein a cap is detachably engaged with the open end.

18. The apparatus of claim 14, wherein the distant portion has an exterior surface, and wherein a plurality of friction enhancing ridges is formed on the exterior surface.

19. The apparatus of claim 14, wherein the distant portion has a pre-determined outer diameter, and wherein a combined surface area of the outwardly flaring front plates is greater than the outer diameter of the distant portion.

20. The apparatus of claim 14, wherein each said outwardly flaring front plate is provided with a narrow point extending forwardly of the distant portion.

21. The apparatus of claim 13, wherein the housing is formed from a fracturable material.

22. The apparatus of claim 13, wherein said plurality of fins is equidistantly secured to the exterior surface of the housing, and wherein channels are formed between adjacent fins.

23. The apparatus of claim 13, wherein each of said plurality of fins has a generally triangular cross-section.

24. A method of dispersing an animal attractant, comprising the steps:
providing a scent dispersing assembly configured for attachment to an arrow, said scent dispersing assembly comprising a frangible housing configured to retain a pre-determined quantity of a liquid scent, said housing having a generally cylindrical hollow body and a plurality of fins secured about an outer periphery of the hollow body and extending outwardly therefrom, said plurality of fins increasing outer dimensions of a forward end of the housing, wherein each of said plurality of fins comprises an outwardly flaring front plate and an attachment member, where the attachment member is integrally formed with the front plate and the housing;
securing the scent dispersing assembly with an arrow;
firing the arrow and causing at least one of the plurality of fins to impact a solid surface without substantially embedding into the solid surface, thereby transmitting impact force to the housing, causing fracture of the housing and dispersing the liquid scent around area of impact.

25. The method of claim 24, further comprising the step of providing an animal attractant as the liquid scent.

26. The method of claim 25, further comprising the step of dispersing the animal attractant from the housing in a fan-like manner.

27. The method of claim 24, further comprising the step of providing threads on said hollow body configured for engagement with the arrow.

28. The method of claim 24, further comprising the step of forming said housing from a fracturable material.

29. The method of claim 24, further comprising a proximate portion of the housing configured for detachable engagement with the arrow, a distant portion carrying the plurality of fins and an intermediate portion formed between the proximate portion and the distant portion.

30. The method of claim 29, further comprising the step of forming said distant portion as a thin-walled enclosure defining a chamber configured to retain a liquid animal attractant.

31. The method of claim 30, further comprising the step of defining the chamber by a sidewall having about 0.76 mm in thickness.

32. The method of claim 29, further comprising the step of providing an open forward end on the distant portion, and a cap detachably engaged with the open end thereby preventing escape of the liquid scent.

33. The method of claim 29, further comprising the step of providing a plurality of friction-enhancing ridges on an exterior surface of the distant portion.

34. The method of claim 29, further comprising the step of providing that the distant portion has a pre-determined outer diameter, and a combined surface area of the outwardly flaring front plates is substantially greater than the outer diameter of the distant portion.

35. The method of claim 29, further comprising the step of providing a narrow point on the outwardly flaring front plate extending forwardly of the distant portion.

36. The method of claim 24, further comprising the step of providing that said plurality of fins increases the outer diameter of a forward end of the housing.

37. The method of claim 24, further comprising the step of providing the plurality of fins be equidistantly secured to the exterior surface of the housing, and further that the channels be formed between adjacent fins.

38. The method of claim 24, further comprising the step of providing each of said plurality of fins with a generally triangular cross-section.

39. The method of claim 24, further comprising the step of retrieving the arrow and the fractured scent dispersing assembly.

40. The method of claim 39, further comprising the step of re-using the arrow with another scent dispersing assembly.

\* \* \* \* \*